US012018150B2

(12) United States Patent
Sarkar et al.

(10) Patent No.: US 12,018,150 B2
(45) Date of Patent: Jun. 25, 2024

(54) ESTER MODIFIED CROSS-LINKED SILICONE COMPOSITIONS

(71) Applicant: Momentive Performance Materials Inc., Waterford, NY (US)

(72) Inventors: Alok Sarkar, Bangalore (IN); Benjamin Falk, Yorktown Heights, NY (US); Ashitha Kandikkal, Bangalore (IN)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 144 days.

(21) Appl. No.: 17/321,257

(22) Filed: May 14, 2021

(65) Prior Publication Data

US 2021/0355325 A1    Nov. 18, 2021

Related U.S. Application Data

(60) Provisional application No. 63/026,399, filed on May 18, 2020.

(51) Int. Cl.

| C08L 83/06 | (2006.01) |
| A61K 8/04 | (2006.01) |
| C08F 220/04 | (2006.01) |
| C08F 230/08 | (2006.01) |
| C08G 77/00 | (2006.01) |
| C08G 77/08 | (2006.01) |
| C08G 77/12 | (2006.01) |
| C08G 77/20 | (2006.01) |
| C08G 77/24 | (2006.01) |
| C08L 83/04 | (2006.01) |

(52) U.S. Cl.
CPC .............. *C08L 83/04* (2013.01); *A61K 8/042* (2013.01); *C08F 220/04* (2013.01); *C08F 230/08* (2013.01); *C08G 77/08* (2013.01); *C08G 77/12* (2013.01); *C08G 77/20* (2013.01); *C08G 77/24* (2013.01); *C08G 77/80* (2013.01); *A61K 2800/10* (2013.01); *A61K 2800/95* (2013.01); *C08L 83/06* (2013.01); *C08L 2312/00* (2013.01)

(58) Field of Classification Search
CPC ......... C08G 77/50; C08G 77/14; C08L 83/14; C08L 83/06
See application file for complete search history.

(56) References Cited

U.S. PATENT DOCUMENTS

| 3,159,601 | A | | 12/1964 | Ashby |
| 3,159,662 | A | | 12/1964 | Ashby |
| 3,220,972 | A | | 11/1965 | Lamoreaux |
| 3,715,334 | A | | 2/1973 | Karstedt |
| 3,775,452 | A | | 11/1973 | Karstedt et al. |
| 3,814,730 | A | | 6/1974 | Karstedt et al. |
| 4,987,169 | A | | 1/1991 | Kuwata et al. |
| 5,654,362 | A | | 8/1997 | Schulz, Jr. et al. |
| 5,760,116 | A | | 6/1998 | Kilgour et al. |
| 5,811,487 | A | | 9/1998 | Schulz, Jr. et al. |
| 6,423,322 | B1 | | 7/2002 | Fry |
| 2004/0147670 | A1 | * | 7/2004 | Hupfield .................... C08J 3/09 |
| | | | | 524/588 |
| 2010/0190871 | A1 | * | 7/2010 | Araki ..................... A61K 8/891 |
| | | | | 514/772.3 |
| 2010/0247460 | A1 | * | 9/2010 | Lin ......................... A61Q 15/00 |
| | | | | 556/400 |
| 2017/0065514 | A1 | * | 3/2017 | Crofoot ................... A61Q 5/02 |

OTHER PUBLICATIONS

International Search Report and Written Opinion for International Application No. PCT/US2021/032567, European Patent Office, Netherlands, dated Aug. 27, 2021, 13 pages.
International Search Report and Written Opinion for International Application No. PCT/US2021/032570, European Patent Office, Netherlands, dated Aug. 27, 2021, 12 pages.
Co-pending Application, U.S. Appl. No. 17/321,250, inventors Sarkar, A., et al., filed May 14, 2021, (Not Published).
Sarkar, A., et al., "Evidence of Cooperativity among van der Waals Interactions in Segmented Polysiloxane," *Macromolecules* 51(22):9354-9359, American Chemical Society, United States (Nov. 2018).
Speier, J.L., "Homogeneous Catalysis of Hydrosilation by Transition Metals," *Advances in Organometallic Chemistry* 17:407-447, Academic Press Inc., United States (1979).

* cited by examiner

*Primary Examiner* — Margaret G Moore
(74) *Attorney, Agent, or Firm* — Sterne, Kessler Goldstein & Fox P.L.L.C.

(57) ABSTRACT

The present disclosures are directed to compositions comprising a polymer having linear or branched silicone substituted by at least one alkylcarboxy group and cross-linked with an alkyl functional cross-linker, which has the benefits of compatibility and structuring of personal care components and the resultant personal care applications.

18 Claims, No Drawings

ESTER MODIFIED CROSS-LINKED SILICONE COMPOSITIONS

BACKGROUND

Field

This invention relates to compositions comprising a polymer having linear or branched silicone substituted by at least one alkylcarboxy group and cross-linked with an alkyl functional cross-linker. In one aspect, personal care compositions containing such carboxyl functional silicone networks are provided herein.

Background

Silicone gels are commonly added in a variety of personal care formulations to enhance their aesthetics with respect to sensory, texture, rheology and optical performance. However, traditional silicone gels have limited versatility in terms of compatibility with polar solvents such as hydrocarbon oils, plant-based oils, glycerin and water. Moreover, most of these gels often fail to retain their texture and rheological benefits at lower dosage. Therefore, there exists a need for a silicone gel composition with improved compatibility, texture and rheological performance.

BRIEF SUMMARY OF THE DISCLOSURE

Compositions comprising a polymer having linear or branched silicone substituted by at least one alkylcarboxy group in a free or salt form and cross-linked with an alkyl functional cross-linker, wherein an average number of alkylcarboxy substitutions per silicone is between 1 and 60 and an average number of crosslinks between linear or branched silicones being between 1 and 30 are described herein. In some aspects, the polymer is a linear polymer. In some aspects, the polymer is a branched polymer.

In some aspects, the average number of alkylcarboxy substitutions per silicone is between 1 and 15. In some aspects, the average number of alkylcarboxy substitutions per silicone is between 1 and 12. In some aspects, the average number of crosslinks between linear or branched silicones is between 1 and 15. In some aspects, the average number of crosslinks between linear or branched silicones is between 1 and 12.

In some aspects, the polymer is prepared by a method comprising reacting:

(a) a Si—H functional compound of formula (I):

wherein:
$M^H = R^1R^2HSiO_{1/2}$;
$M = R^3R^4R^5SiO_{1/2}$;
$D^H = R^6HSiO_{2/2}$;
$D = R^7R^8SiO_{2/2}$;
$T^H = HSiO_{3/2}$;
$T = R^9SiO_{3/2}$; and
$Q = SiO_{4/2}$;
wherein
$R^1, R^2, R^3, R^4, R^5, R^6, R^7, R^8$, and $R^9$ are independently an aliphatic, aromatic, or fluoro monovalent hydrocarbon having from 1 to 60 carbon atoms; and
a, b, c, d, e, f, and g are independently zero or a positive integer, such that $2 \leq a+b+c+d+e+f+g \leq 6000$ and when $a'+c'+e'=2$, $a+c+e>2$;

(b) a carboxy functional olefin of formula (II):

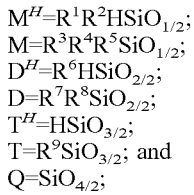

wherein
R' is hydrogen, $-Si(R^a)_3$ wherein $R^a$ is an aliphatic monovalent hydrocarbon, or an aliphatic, aromatic or fluoro monovalent hydrocarbon;
n is $0 \leq n \leq 30$; and (c) a silicone based alkenyl functional cross-linker of formula (III) and/or a non-silicone based alkenyl functional cross-linker of formula (IV):

$$M^1{}_{a'}M^2{}_{b'}D^1{}_{c'}D^2{}_{d'}T^1{}_{e'}T^2{}_{f'}Q_{g'} \quad (III),$$

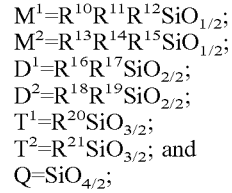

wherein:
$M^1 = R^{10}R^{11}R^{12}SiO_{1/2}$;
$M^2 = R^{13}R^{14}R^{15}SiO_{1/2}$;
$D^1 = R^{16}R^{17}SiO_{2/2}$;
$D^2 = R^{18}R^{19}SiO_{2/2}$;
$T^1 = R^{20}SiO_{3/2}$;
$T^2 = R^{21}SiO_{3/2}$; and
$Q = SiO_{4/2}$;
wherein
$R^{11}, R^{12}, R^{13}, R^{14}, R^{15}, R^{17}, R^{18}, R^{19}$, and $R^{21}$, are independently an aliphatic, aromatic, or fluoro monovalent hydrocarbon having from 1 to 60 carbon atoms;
$R^{10}, R^{16}$, and $R^{20}$ are each a monovalent radical containing at least one terminal olefin bond wherein a', b', c', d', e', f', and g' are independently zero or a positive integer, such that $2 \leq a'+b'+c'+d'+e'+f'+g' \leq 6000$ and when $a+c+e=2$, $a'+c'+e'>2$; and
Z is an aliphatic hydrocarbon with 1 to 60 carbon atoms.

The polymer can be prepared by mixing the components in any order. Additionally, each component can be added simultaneously or sequentially, or as batch or semi-batch preparations.

The disclosure also relates to methods for preparing the polymer comprising reacting:

(a) a Si—H functional compound of formula (I):

wherein:
$M^H = R^1R^2HSiO_{1/2}$;
$M = R^3R^4R^5SiO_{1/2}$;
$D^H = R^6HSiO_{2/2}$;
$D = R^7R^8SiO_{2/2}$;
$T^H = HSiO_{3/2}$;
$T = R^9SiO_{3/2}$; and
$Q = SiO_{4/2}$;
wherein
$R^1, R^2, R^3, R^4, R^5, R^6, R^7, R^8$, and $R^9$ are independently an aliphatic, aromatic, or fluoro monovalent hydrocarbon having from 1 to 60 carbon atoms; and
a, b, c, d, e, f, and g are independently zero or a positive integer, such that $2 \leq a+b+c+d+e+f+g \leq 6000$ and when $a'+c'+e'=2$, $a+c+e>2$;

(b) a carboxy functional olefin of formula (II):

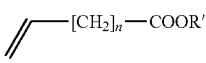  (II)

wherein
R' is hydrogen, —Si(R$^a$)$_3$ wherein R$^a$ is an aliphatic monovalent hydrocarbon, or an aliphatic, aromatic or fluoro monovalent hydrocarbon;
n is 0≤n≤30; and (c) a silicone based alkenyl functional cross-linker of formula (III) and/or a non-silicone based alkenyl functional cross-linker of formula (IV):

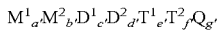  (III),

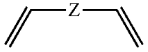  (IV)

wherein:
$M^1 = R^{10}R^{11}R^{12}SiO_{1/2}$;
$M^2 = R^{13}R^{14}R^{15}SiO_{1/2}$;
$D^1 = R^{16}R^{17}SiO_{2/2}$;
$D^2 = R^{18}R^{19}SiO_{2/2}$;
$T^1 = R^{20}SiO_{3/2}$;
$T^2 = R^{21}SiO_{3/2}$; and
$Q = SiO_{4/2}$;
wherein
$R^{11}$, $R^{12}$, $R^{13}$, $R^{14}$, $R^{15}$, $R^{17}$, $R^{18}$, $R^{19}$, and $R^{21}$, are independently an aliphatic, aromatic, or fluoro monovalent hydrocarbon having from 1 to 60 carbon atoms;
$R^{10}$, $R^{16}$ and $R^{20}$ are each a monovalent radical containing at least one terminal olefin bond;
a', b', c', d', e', f', and g' are independently zero or a positive integer, such that 2≤a'+b'+c'+d'+e'+f'+g'≤6000 and when a+c+e=2, a'+c'+e'>2; and
Z is an aliphatic hydrocarbon with 1 to 60 carbon atoms.

The polymer can be prepared by mixing the components in any order. Additionally, each component can be added simultaneously or sequentially, or as batch or semi-batch preparations.

In some aspects, the reaction between the Si—H compound of formula (I), the carboxy functional olefin of formula (II) and the alkenyl functional cross-linker of formula (III) and/or (IV) occurs in the presence of at least one precious metal catalyst selected from the group consisting of a rhodium, ruthenium, palladium, osmium, iridium, iron, and platinum catalyst. In some aspects, at least one of the platinum catalysts is selected from the group consisting of (PtCl2Olefin), H(PtCl3Olefin), platinic chloride, chloroplatinic acid, bis(acetylacetonato)platinum, (η15-Cyclopentadienyl)trialkylplatinum, 1,3-bis(2,6-diisopropylphenyl)imidazol-2-ylidene-1,3-divinyl-1,1,3,3-tetramethyldisiloxaneplatinum(0), 1,3-bis(cyclohexyl)imidazole-2-ylidene-1,3-divinyl-1,1,3,3-tetramethyldisiloxaneplatinum(0), Pt$_2$(dba)$_3$, Pt$_2$(dvs)$_3$, Pt(OAc)$_2$, Pt(acac)$_2$, Na$_2$PtCl$_6$, K$_2$PtCl$_6$, platinum carbonate, platinum nitrate, 1,5-cyclooctadienedimethylplatinum (II), platinum perchlorate, amine complexes of the platinum ammonium hexachloropalladate(IV), a cyclopropane complex of platinum chloride, and a complex formed from chloroplatinic acid.

In some aspects, one or more of $R^1$, $R^2$, $R^3$, $R^4$, $R^5$, $R^6$, $R^7$, $R^8$, and $R^9$ is an aliphatic, aromatic, or fluoro monovalent hydrocarbon. In some aspects, one or more of $R^1$, $R^2$, $R^3$, $R^4$, $R^5$, $R^6$, $R^7$, $R^8$, and $R^9$ is a $C_1$-$C_{60}$ monovalent hydrocarbon. In some aspects, one or more of $R^1$, $R^2$, $R^3$, $R^4$, $R^5$, $R^6$, $R^7$, $R^8$, and $R^9$ is a $C_1$-$C_{20}$ monovalent hydrocarbon. In some aspects, one or more of $R^1$, $R^2$, $R^3$, $R^4$, $R^5$, $R^6$, $R^7$, $R^8$, and $R^9$ is a $C_1$-$C_8$ monovalent hydrocarbon.

In some aspects, a, b, c, d, e, f, and g are 2≤a+b+c+d+e+f+g≤4000. In some aspects, a, b, c, d, e, f, and g are 2≤a+b+c+d+e+f+g≤2000. In some aspects, a, c, and e are 2≤a+c+e≤120. In some aspects, a, c, and e are 2≤a+c+e≤100.

In some aspects, R' is $R^1$ or a combination of $R^1$ and —Si(R$^a$)$_3$ wherein R$^a$ is an aliphatic monovalent hydrocarbon. In some aspects, R$^a$ is a $C_1$-$C_{12}$ group. In some aspects, R$^a$ is a $C_1$-$C_8$ group. In some aspects, R$^a$ is selected from the group consisting of methyl, ethyl, propyl, butyl, pentyl, hexyl, and heptyl. In some aspects, R$^a$ is methyl. In some aspects, R' is ethyl. In some aspects, R' is heptyl. In some aspects, R' is hydrogen.

In some aspects, $R^{11}$, $R^{12}$, $R^{13}$, $R^{14}$, $R^{15}$, $R^{17}$, $R^{18}$, $R^{19}$, and $R^{21}$, are independently an aliphatic, aromatic, or fluoro monovalent hydrocarbon having from 1 to 60 carbon atoms. In some aspects, one or more of $R^{11}$, $R^{12}$, $R^{13}$, $R^{14}$, $R^{15}$, $R^{17}$, $R^{18}$, $R^{19}$, and $R^{21}$ is a $C_1$-$C_{30}$ monovalent hydrocarbon. In some aspects, one or more of $R^{11}$, $R^{12}$, $R^{13}$, $R^{14}$, $R^{15}$, $R^{17}$, $R^{18}$, $R^{19}$, and $R^{21}$ is a $C_1$-$C_{18}$ monovalent hydrocarbon.

In some aspects, one or more of $R^{11}$, $R^{12}$, $R^{13}$, $R^{14}$, $R^{15}$, $R^{17}$, $R^{18}$, $R^{19}$, and $R^{21}$ is an aliphatic monovalent hydrocarbon. In some aspects, one or more of $R^{11}$, $R^{12}$, $R^{13}$, $R^{14}$, $R^{15}$, $R^{17}$, $R^{18}$, $R^{19}$, and $R^{21}$ is selected from the group consisting of methyl, ethyl, n-propyl, isopropyl, n-butyl, isobutyl, tert-butyl, n-pentyl, isopentyl, neo-pentyl, tert-pentyl, hexyl, heptyl, octyl, nonyl, decyl, and cycloalkyl. In some aspects, one or more of $R^{11}$, $R^{12}$, $R^{13}$, $R^{14}$, $R^{15}$, $R^{17}$, $R^{18}$, $R^{19}$, and $R^{21}$ is selected from the group consisting of n-hexyl, n-heptyl, n-octyl, isooctyl, 2,2,4-trimethylpentyl, n-nonyl, n-decyl, cyclopentyl, cyclohexyl, cycloheptyl, and methylcyclohexyl.

In some aspects, one or more of $R^{11}$, $R^{12}$, $R^{13}$, $R^{14}$, $R^{15}$, $R^{17}$, $R^{18}$, $R^{19}$, and $R^{21}$ is an aromatic monovalent hydrocarbon. In some aspects, one or more of $R^{11}$, $R^{12}$, $R^{13}$, $R^{14}$, $R^{15}$, $R^{17}$, $R^{18}$, $R^{19}$, and $R^{21}$ is selected from the group consisting of phenyl, naphthyl, o-tolyl, m-tolyl, p-tolyl, xylyl, ethylphenyl, and benzyl.

In some aspects, one or more of $R^{11}$, $R^{12}$, $R^{13}$, $R^{14}$, $R^{15}$, $R^{17}$, $R^{18}$, $R^{19}$, and $R^{21}$ is a fluoro monovalent hydrocarbon.

In some aspects, a'=2, d'=75-600, and b'=c'=e'=f'=g'=0. In some aspects, a', c', and e' are 2≤a'+c'+e'≤120. In some aspects, a', c', and e' are 2≤a'+c'+e'≤100. In some aspects, a=12, b=c=d=e=f=0, g=10, and n=8. In some aspects, b=2, c=36, a=d=e=f=g=0, and n=8. In some aspects, a=3, b=c=d=e=g=0, f=1, and n=8.

In some aspects, Z is —(CHR$^{22}$)$_m$— or —(CH$_2$CHR$^{23}$O)$_k$—, and m and k are positive integers, such that 1≤m≤60 and 1≤k≤500, and $R^{22}$ and $R^{23}$ are independently hydrogen or monovalent hydrocarbon having from 1 to 60 carbon atoms. In some aspects, Z is —(CHR$^{22}$)$_m$—, m is 1-30, and $R^{22}$ is from 1 to 30 carbon atoms. In some aspects, Z is —(CHR$^{22}$)$_m$—, m is 1-18, and $R^{16}$ is from 1 to 20 carbon atoms. In some aspects, Z is —(CH$_2$CHR$^{23}$O)$_k$—, k is 1-250, and $R^{23}$ is from 1 to 30 carbon atoms. In some aspects, Z is —(CH$_2$CHR$^{23}$O)$_k$—, k is 1-100, and $R^{23}$ is from 1 to 20 carbon atoms.

In some aspects, the polymer is in a pure carboxy alkyl ester form. In some aspects, the polymer is in combination of a carboxy alkyl ester and salt (or acid) form. In some aspects, a cation of the salt form is independently selected from alkali metals, alkaline earth metals, transition metals, rare earth metals, metals, metal complexes, quaternary ammonium and phosphonium groups, organic cations, alkyl cations, cationic hydrocarbons, cationic polymers, or zwitterions.

The disclosure also relates to a product prepared by any of the methods described herein.

The disclosure additionally relates to personal care compositions comprising (a) a composition or product described herein; and (b) one or more personal care components.

In some aspects, the one or more personal care components are selected from the group consisting of a humectant, emollient, moisturizer, pigment, colorant, fragrance, biocide, preservative, antioxidant, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, and thickening agent. In some aspects, the one or more emollients is selected from the group consisting of triglyceride esters, wax esters, alkyl or alkenyl ester of fatty acids, polyhydric alcohol esters, and mixtures thereof. In some aspects, the one or more personal care components is a silicone oil, an organic oil, or mixtures thereof.

The disclosure further relates to a personal care application comprising a personal care component described herein, wherein the personal care application is selected from the group consisting of a deodorant, antiperspirant, antiperspirant/deodorant, shaving product, skin lotion, moisturizer, toner, bath product, cleansing product, hair care product, manicure product, protective cream, and color cosmetic.

DETAILED DESCRIPTION

Definitions and Abbreviations

As used above, and throughout the description, the following terms, unless otherwise indicated, shall be understood to have the following meanings.

Unless stated otherwise, the terms "a" and "an" and "the" and similar references used in the context of describing a particular aspect of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein.

The term "carboxy" means the radical —C(O)O—. It is noted that compounds described herein containing carboxy moiety can include protected derivatives thereof, i.e., where the oxygen is substituted with a protecting group. Suitable protecting groups for carboxy moieties include benzyl, tert-butyl, methyl, ethyl, and the like. The term "carboxyl" means —COOH.

The term "polymer" means a substance, chemical compound or mixture of compounds, that has a molecular structure consisting chiefly or entirely of a large number of similar units (e.g., monomer units) bonded together.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "aliphatic monovalent hydrocarbon" as used herein, means hydrocarbon which is completely saturated and is not aromatic. For example, suitable aliphatic groups include linear alkyl groups. A "fluoro monovalent hydrocarbon" means a completely saturated hydrocarbon that is substituted with a fluoro atom.

The term "pure" as used herein, means free of any contamination or not mixed or adulterated with any other substance or material. For example, a pure carboxy alkyl ester form refers to a substance, material, or polymer with at least one ester functional group only.

The term "hydrocarbon" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group. Examples of "alkyl" groups include methyl, ethyl, isopropyl, and the like.

The term "aromatic" refer to an optionally substituted $C_{6-14}$ aromatic hydrocarbon moiety comprising one to three aromatic rings. In at least one aspect, the aromatic group is a $C_{6-10}$ aryl group. Aromatic groups include, without limitation, phenyl. The term "aromatic" can be used interchangeably with the terms "aryl group," "aryl ring," and "aryl."

In describing the products as a reaction product of initial materials, reference is made to the initial species recited and it is to be noted that additional materials can be added to the initial mixture of synthetic precursors. These additional materials can be reactive or non-reactive. The defining characteristic is that the reaction product can be obtained from the reaction of at least the components listed as disclosed. Non-reactive components can be added to the reaction mixture as diluents or to impart additional properties unrelated to the properties of the composition prepared as a reaction product. Thus, for example particulate solids, such as pigments, can be dispersed into the reaction mixture, before, during, or after the reaction to produce a reaction product composition that additionally comprises the non-reactive component. Additional reactive components can also be added. Such components can react with the initial reactants or they can react with the reaction product. The phrase "reaction product" is intended to include those possibilities, as well as including the addition of non-reactive components.

The expression "shearing" as used herein means the silicone composition can be further processed to adjust the viscosity and sensory feel of the composition. This can be achieved, for example, by subjecting the composition to a moderate to high shearing force.

As used herein, the term "non-aqueous hydroxylic organic compound" or "non-aqueous hydroxylic solvent" means hydroxyl containing organic compounds such as, but not limited to, alcohols, glycols, polyhydric alcohols and polymeric glycols and mixtures thereof, that are liquid at room temperature, e.g. about 25° C., and about one atmosphere pressure.

Polymeric Compositions

Compositions comprising a polymer having linear or branched silicone substituted by at least one alkylcarboxy group in a free or salt form and cross-linked with an alkyl functional cross-linker, wherein an average number of alkyl-carboxy substitutions per silicone is between 1 and 60 and an average number of crosslinks between linear or branched silicones being between 1 and 30 are described herein. In some aspects, the polymer is a linear polymer. In some aspects, the polymer is a branched polymer.

In some aspects, the average number of alkylcarboxy substitutions per silicone is between 1 and 15. In some aspects, the average number of alkylcarboxy substitutions per silicone is between 1 and 12. In some aspects, the average number of alkylcarboxy substitutions per silicone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60.

In some aspects, the average number of crosslinks between linear or branched silicones is between 1 and 15. In some aspects, the average number of crosslinks between linear or branched silicones is between 1 and 12. In some aspects, the average number of crosslinks between linear or branched silicones is 1, 2, 3, 4, 5, 6, 7, 8, 9, 10, 11, or 12.

In some aspects, the polymer is prepared by a method comprising reacting:

(a) a Si—H functional compound of formula (I):

     (I)

wherein:
$M^H = R^1R^2HSiO_{1/2}$;
$M = R^3R^4R^5SiO_{1/2}$;
$D^H = R^6HSiO_{2/2}$;
$D = R^7R^8SiO_{2/2}$;
$T^H = HSiO_{3/2}$;
$T = R^9SiO_{3/2}$; and
$Q = SiO_{4/2}$;

wherein
$R^1, R^2, R^3, R^4, R^5, R^6, R^7, R^8$, and $R^9$ are independently an aliphatic, aromatic, or fluoro monovalent hydrocarbon having from 1 to 60 carbon atoms; and a, b, c, d, e, f, and g are independently zero or a positive integer, such that $2 \leq a+b+c+d+e+f+g \leq 6000$ and when $a'+c'+e'=2$, $a+c+e>2$;

(b) a carboxy functional olefin of formula (II):

     (II)

wherein
R' is hydrogen, —Si(R$^a$)$_3$ wherein R$^a$ is an aliphatic monovalent hydrocarbon, or an aliphatic, aromatic or fluoro monovalent hydrocarbon;
n is $0 \leq n \leq 30$; and (c) a silicone based alkenyl functional cross-linker of formula (III) and/or a non-silicone based alkenyl functional cross-linker of formula (IV):

     (III),

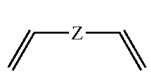     (IV)

wherein:
$M^1 = R^{10}R^{11}R^{12}SiO_{1/2}$;
$M^2 = R^{13}R^{14}R^{15}SiO_{1/2}$;
$D^1 = R^{16}R^{17}SiO_{2/2}$;
$D^2 = R^{18}R^{19}SiO_{2/2}$;
$T^1 = R^{20}SiO_{3/2}$;
$T^2 = R^{21}SiO_{3/2}$; and
$Q = SiO_{4/2}$;

wherein
$R^{11}, R^{12}, R^{13}, R^{14}, R^{15}, R^{17}, R^{18}, R^{19}$, and $R^{21}$, are independently an aliphatic, aromatic, or fluoro monovalent hydrocarbon having from 1 to 60 carbon atoms;
$R^{10}$, $R_{16}$, and $R^{20}$ are each a monovalent radical containing at least one terminal olefin bond; a', b', c', d', e', f', and g' are independently zero or a positive integer, such that $2 \leq a'+b'+c'+d'+e'+f'+g' \leq 6000$ and when $a+c+e=2$, $a'+c'+e'>2$; and
Z is an aliphatic hydrocarbon with 1 to 60 carbon atoms.

The polymer can be prepared by mixing the components in any order. Additionally, each component can be added simultaneously or sequentially, or as batch or semi-batch preparations.

The reaction between the Si—H functional compound of formula (I), carboxy functional olefin of formula (II), and silicone based alkenyl functional cross-linker of formula (III) and/or non-silicone based alkenyl functional cross-linker of formula (IV) occurs in the presence of a suitable solvent. The suitable solvent can be a low viscosity silicone fluid or a volatile silicone fluid. Examples of suitable solvents include, but are not limited to isodecane, isohexadecane, squalane, hemisqualane, hydrogenated polyisobutene, jojoba, cylcopentasiloxane, dimethicone, bis-phenylpropyl dimethicone, octyldodecyl neopentanoate, oleyl oleate, oleyl alcohol, isomyristyl alcohol, or combinations thereof.

In some aspects, the reaction between the Si—H compound of formula (I), the carboxy functional olefin of formula (II) and the alkenyl functional cross-linker of formula (III) and/or (IV) occurs in the presence of at least one precious metal catalyst selected from the group consisting of a rhodium, ruthenium, palladium, osmium, iridium, iron, and platinum catalyst. In some aspects, at least one of the platinum catalysts is selected from the group consisting of (PtCl$_2$Olefin), H(PtCl$_3$Olefin), platinic chloride, chloroplatinic acid, bis(acetylacetonato)platinum, (η15-Cyclopentadienyl)trialkylplatinum, 1,3-bis(2,6-diisopropylphenyl)imidazol-2-ylidene-1,3-divinyl-1,1,3,3-tetramethyldisiloxaneplatinum(0), 1,3-bis(cyclohexyl) imidazole-2-ylidene-1,3-divinyl-1,1,3,3-tetramethyldisiloxaneplatinum(0), Pt$_2$(dba)$_3$, Pt$_2$(dvs)$_3$, Pt(OAc)$_2$, Pt(acac)$_2$, Na$_2$PtCl$_6$, K$_2$PtCl$_6$, platinum carbonate, platinum nitrate, 1,5-cyclooctadienedimethylplatinum (II), platinum perchlorate, amine complexes of the platinum ammonium hexachloropalladate(IV), a cyclopropane complex of platinum chloride, and a complex formed from chloroplatinic acid.

In some aspects, the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts most specifically used herein are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in Advances in Organometallic Chemistry, volume 17, pages 407 through 447, F. G. A. Stone and R. West editors, published by the Academic Press (New York, 1979). In some aspects, the platinum catalyst is a soluble complex form.

The amount of precious metal catalyst utilized in the reaction can range from between about 0.1 and about 10,000 ppm. In some aspects, the amount of precious metal catalyst can range from between about 1 and about 1,000 ppm. In some aspects, the amount of precious metal catalyst can range from between about 1 and 500 ppm. In some aspects, the amount of precious metal catalyst can range from between about 1 and 250 ppm. In some aspects, the amount of precious metal catalyst can range from between about 1 and 100 ppm.

In some aspects, one or more of $R^1$, $R^2$, $R^3$, $R^4$, $R^5$, $R^6$, $R^7$, $R^8$, and $R^9$ is an aliphatic, aromatic, or fluoro monovalent hydrocarbon. In some aspects, one or more of $R^1$, $R^2$, $R^3$, $R^4$, $R^5$, $R^6$, $R^7$, $R^8$, and $R^9$ is a $C_1$-$C_{30}$ monovalent hydrocarbon. In some aspects, one or more of $R^1$, $R^2$, $R^3$, $R^4$, $R^5$, $R^6$, $R^7$, $R^8$, and $R^9$ is a $C_1$-$C_{18}$ monovalent hydrocarbon. In some aspects, one or more of $R^1$, $R^2$, $R^3$, $R^4$, $R^5$, $R^6$, $R^7$, $R^8$, and $R^9$ is a $C_1$-$C_{12}$ or $C_1$-$C_6$ monovalent hydrocarbon. Examples of monovalent hydrocarbons for $R^1$, $R^2$, $R^3$, $R^4$, $R^5$, $R^6$, $R^7$, $R^8$, and $R^9$ isopropyl, n-butyl, isobutyl, tert-butyl, n-pentyl, isopentyl, neo-pentyl, tert-pentyl, hexyl (e.g., n-hexyl), heptyl (e.g., n-heptyl), octyl (e.g., n-octyl, isocytyl), 2,2,4-trimethylpentyl, nonyl (n-decyl), decyl, cycloalkyl (e.g., cyclopentyl, cyclohexyl, cycloheptyl, and methylcyclohexyl), phenyl, naphthyl, o-tolyl, m-tolyl, p-tolyl, xylyl, ethylphenyl, benzyl, any of which can be optionally substituted by one or more fluoro atoms.

In some aspects, a, b, c, d, e, f, and g are $2 \leq a+b+c+d+e+f+g \leq 4000$. In some aspects, a, b, c, d, e, f, and g are $2 \leq a+b+c+d+e+f+g \leq 2000$. In some aspects, a, b, c, d, e, f, and g are $2 \leq a+b+c+d+e+f+g \leq 1000$. In some aspects, a, b, c, d, e, f, and g are $2 \leq a+b+c+d+e+f+g \leq 1500$. In some aspects, a, b, c, d, e, f, and g are $2 \leq a+b+c+d+e+f+g \leq 250$. In some aspects, a, c, and e are $2 \leq a+c+e \leq 120$. In some aspects, a, c, and e are $2 \leq a+c+e \leq 100$.

In some aspects, R' is $R^1$ or a combination of $R^1$ and $-Si(R^a)_3$ wherein $R^a$ is an aliphatic monovalent hydrocarbon. In some aspects, $R^a$ is a $C_1$-$C_{12}$ group. In some aspects, $R^a$ is a $C_1$-$C_8$ group. In some aspects, $R^a$ is selected from the group consisting of methyl, ethyl, propyl (n-propyl or iso-propyl), butyl (e.g. n-butyl, tert-butyl), pentyl (e.g., n-pentyl, isopentyl), hexyl (e.g., n-hexyl), and heptyl (e.g., n-heptyl). In some aspects, $R^a$ is methyl. In some aspects, R' is ethyl. In some aspects, R' is heptyl. In some aspects, R' is hydrogen.

In some aspects, $R^{11}$, $R^{12}$, $R^{13}$, $R^{14}$, $R^{15}$, $R^{17}$, $R^{18}$, $R^{19}$, and $R^{21}$, are independently an aliphatic, aromatic, or fluoro monovalent hydrocarbon having from 1 to 60 carbon atoms. In some aspects, one or more of $R^{11}$, $R^{12}$, $R^{13}$, $R^{14}$, $R^{15}$, $R^{17}$, $R^{18}$, $R^{19}$, and $R^{21}$ is a $C_1$-$C_{30}$ monovalent hydrocarbon. In some aspects, one or more of $R^{11}$, $R^{12}$, $R^{13}$, $R^{14}$, $R^{15}$, $R^{17}$, $R^{18}$, $R^{19}$, and $R^{21}$ is a $C_1$-$C_{18}$ monovalent hydrocarbon.

In some aspects, one or more of $R^{11}$, $R^{12}$, $R^{13}$, $R^{14}$, $R^{15}$, $R^{17}$, $R^{18}$, $R^{19}$, and $R^{21}$ an aliphatic monovalent hydrocarbon. In some aspects, one or more of $R^{11}$, $R^{12}$, $R^{13}$, $R^{14}$, $R^{15}$, $R^{17}$, $R^{18}$, $R^{19}$, and $R^{21}$ is selected from the group consisting of methyl, ethyl, n-propyl, isopropyl, n-butyl, isobutyl, tert-butyl, n-pentyl, isopentyl, neo-pentyl, tert-pentyl, hexyl, heptyl, octyl, nonyl, decyl, and cycloalkyl. In some aspects, one or more of $R^{11}$, $R^{12}$, $R^{13}$, $R^{14}$, $R^{15}$, $R^{17}$, $R^{18}$, $R^{19}$, and $R^{21}$ is selected from the group consisting of n-hexyl, n-heptyl, n-octyl, isooctyl, 2,2,4-trimethylpentyl, n-nonyl, n-decyl, cyclopentyl, cyclohexyl, cycloheptyl, and methylcyclohexyl.

In some aspects, one or more of $R^{11}$, $R^{12}$, $R^{13}$, $R^{14}$, $R^{15}$, $R^{17}$, $R^{18}$, $R^{19}$, and $R^{21}$ is an aromatic monovalent hydrocarbon. In some aspects, one or more of $R^{11}$, $R^{12}$, $R^{13}$, $R^{14}$, $R^{15}$, $R^{17}$, $R^{18}$, $R^{19}$, and $R^{21}$ is selected from the group consisting of phenyl, naphthyl, o-tolyl, m-tolyl, p-tolyl, xylyl, ethylphenyl, and benzyl.

In some aspects, one or more of $R^{11}$, $R^{12}$, $R^{13}$, $R^{14}$, $R^{15}$, $R^{17}$, $R^{18}$, $R^{19}$, and $R^{21}$ is a fluoro monovalent hydrocarbon.

In some aspects, a', b', c', d', e', f', and g' are $2 \leq a'+b'+c'+d'+e'+f'+g' \leq 4000$. In some aspects, a', b', c', d', e', f', and g' are $2 \leq a'+b'+c'+d'+e'+f'+g' \leq 3000$. In some aspects, a', b', c', d', e', f', and g' are $2 \leq a'+b'+c'+d'+e'+f'+g' \leq 2000$. In some aspects, a', b', c', d', e', f', and g' are $2 \leq a'+b'+c'+d'+e'+f'+g' \leq 1000$. In some aspects, a', b', c', d', e', f, and g' are $2 \leq a'+b'+c'+d'+e'+f'+g' \leq 500$. In some aspects, a', c', and e' are $2 \leq a'+c'+e' \leq 120$. In some aspects, a', c', and e' are $2 \leq a'+c'+e' \leq 100$. In some aspects, a'=2, d'=75-600, and b'=c'=e'=f'=g'=0.

In some aspects, Z is $-(CHR^{22})_m-$ or $-(CH_2CHR^{23}O)_k-$, and m and k are positive integers, such that $1 \leq m \leq 60$ and $1 \leq k \leq 500$, and $R^{22}$ and $R^{23}$ are independently hydrogen or monovalent hydrocarbon having from 1 to 60 carbon atoms. In some aspects, Z is $-(CHR^{22})_m-$, m is 1-30, and $R^{22}$ is from 1 to 30 carbon atoms. In some aspects, Z is $-(CHR^{22})_m-$, m is 1-18, and $R^{16}$ is from 1 to 20 carbon atoms. In some aspects, Z is $-(CH_2CHR^{23}O)_k-$, k is 1-250, and $R^{23}$ is from 1 to 30 carbon atoms. In some aspects, Z is $-(CH_2CHR^{23}O)_k-$, k is 1-100, and $R^{23}$ is from 1 to 20 carbon atoms.

In some aspects, the polymer is in a pure carboxy alkyl ester form. In some aspects, the polymer is in combination of a carboxy alkyl ester and salt (or acid) form. In some aspects, a cation of the salt form is independently selected from alkali metals, alkaline earth metals, transition metals, rare earth metals, metals, metal complexes, quaternary ammonium and phosphonium groups, organic cations, alkyl cations, cationic hydrocarbons, cationic polymers, or zwitterions.

The disclosure also relates to a product prepared by any of the methods described herein.

Personal Care Compositions

The disclosure additionally relates to personal care compositions comprising (a) a composition or product described herein; and (b) one or more personal care components. In one aspect, the personal care composition comprises a solvent.

In one aspect herein, the silicone compositions described herein are self-emulsifying. In another aspect, the personal care composition may be further processed under low to high shear to adjust the viscosity and sensory feel of the composition. This can be achieved, for example, by subjecting the composition to a moderate to high shearing force. High shear may be applied using, for example, a Sonolator apparatus, a Gaulin Homogenizer or a Micro Fluidizer apparatus. One or more carrier solvent may be added to the silicone composition prior to the shearing.

In one aspect, the personal care composition is a solid, typically having a creamy consistency, wherein the silicone polymer acts as a means for gelling the fluid to reversibly impart characteristics of a solid to the fluid. At rest, the personal care composition exhibits the properties of a solid gel material. The personal care composition can exhibit high stability and resistance to syneresis so that the personal care composition exhibits little or no tendency for fluid to flow from the personal care composition. The high stability and syneresis resistance persists with prolonged aging of the personal care compositions.

However, the solvent included in the personal care composition can be released from the polymers described herein by subjecting the personal care composition to a shearing force, such as, for example, by rubbing the composition between one's fingers, to provide improved sensory feel characteristic of the fluid component of the silicone material. Water (or a water equivalent such as a non-aqueous hydroxylic solvent), siloxane, hydrocarbon, linear or cyclic, or lipophilic fluid (oil swelling agent, oil swellable) can be used as the solvent which may function as a swelling agent. Lipophilic fluids suitable for use as the solvent component of the personal care composition are those described herein. In one aspect, the solvent component of the personal care composition exhibits a viscosity of below 1,000 cSt. In one aspect, the solvent component of the personal care composition exhibits a viscosity below 500 cSt. In one aspect, the solvent component of the personal care composition exhibits a viscosity of below 250 cSt. In one aspect, the solvent component of the personal care composition exhibits a viscosity of below 100 cSt, at 25° C.

In one aspect, the polymers described herein are soluble in various fluid components, and are capable of thickening the solvent. The amount of crosslinking present in the polymers described herein may be characterized with respect to the degree of thickening exhibited by the polymer in the solvent.

In another aspect, the cross linked structure of the polymers described herein is effective to allow the polymer to be swollen by a low molecular weight fluid, such as a silicone fluid, hydrophobic oil, or silicone and hydrocarbon fluid, such as, for example, decamethylcyclopentasiloxane, from its original volume to a swollen volume.

The polymers described herein can be utilized as prepared or as the hydrophobic component in a personal care composition that is an emulsion. Emulsions comprise at least two immiscible phases. One immiscible phase is continuous and the other is discontinuous. In one aspect, the non-miscible phase (immiscible phase) is aqueous, non-aqueous, or solid particulates.

Emulsions can be liquids with varying viscosities or solids. The particle size of the emulsions can make them microemulsions. When sufficiently small, the microemulsions can be transparent. It is also possible to prepare emulsions of emulsions which are generally known as multiple emulsions.

Examples of suitable emulsions for personal care compositions include: 1) aqueous emulsions where the discontinuous phase comprises water and the continuous phase comprises a polymer composition or product described herein; 2) aqueous emulsions where the discontinuous phase comprises a polymer composition or product described herein and the continuous phase comprises water; 3) non-aqueous emulsions where the discontinuous phase comprises a non-aqueous hydroxylic solvent and the continuous phase comprises a polymer composition or product described herein; and 4) non-aqueous emulsions where the continuous phase comprises a non-aqueous hydroxylic organic solvent and the discontinuous phase comprises a polymer composition or product described herein.

Examples of suitable non-aqueous hydroxylic organic solvents in the emulsions containing a polymer composition or product described herein include, but are not limited to, ethylene glycol, ethanol, propyl alcohol, isopropyl alcohol, propylene glycol, dipropylene glycol, tripropylene glycol, butylene glycol, isobutylene glycol, methyl propane diol, glycerin, sorbitol, polyethylene glycol, polypropylene glycol mono alkyl ethers, polyoxyalkylene copolymers and mixtures thereof.

In one aspect, the polymers described herein are compatible with a particulate additive. In one aspect, the particulate additive is an inorganic particulate, polymeric latex, and/or a pigment. In another aspect, the polymers are capable of suspending these particles for a prolonged period in personal care formulations.

Once the desired emulsion is prepared, the resulting material is usually a high viscosity cream with good feel characteristics and high absorbance of volatile solvents. The emulsion can then be blended into personal care compositions for hair care, skin care, and the like.

The personal care composition can be a personal care application including deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products (e.g., nail polish, nail polish remover, nail creams and lotions, cuticle softeners), protective creams (e.g., sunscreen, insect repellent and anti-aging products), color cosmetics (e.g., lipsticks, foundations, face powders, eye liners, eye shadows, blushes, makeup, and mascaras). The personal care application can also be a drug delivery system for topical application of a medicinal composition that can be applied to the skin.

In one aspect, the personal care composition of the present invention further comprises one or more personal care ingredients. Suitable personal care ingredients include, for example, emollients, moisturizers, humectants, pigments (e.g., pearlescent pigments such as bismuth oxychloride and titanium dioxide coated mica), colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents (e.g., fumed silica or hydrated silica), particulate fillers (e.g., talc, kaolin, starch, modified starch, mica, nylon, clays, such as, for example, bentonite and organo-modified clays).

In some aspects, the one or more personal care components included in the personal care compositions are selected from the group consisting of a humectant, emollient, moisturizer, pigment, colorant, fragrance, biocide, preservative, antioxidant, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, and thickening agent. In some aspects, the one or more emollients is selected from the group consisting of triglyceride esters, wax esters, alkyl or alkenyl ester of fatty acids, polyhydric alcohol esters, and mixtures thereof. In some aspects, the one or more personal care components is a silicone oil, an organic oil, or mixtures thereof.

In one aspect, the personal care composition is an antiperspirant composition that comprises a polymer composition or product described herein and one or more active antiperspirant agents. Suitable antiperspirant agents include, but are not limited to, the Category I active antiperspirant ingredients listed in the U.S. Food and Drug Administration's Oct. 10, 1993 Monograph on antiperspirant drug products for over-the-counter human use including aluminum halides, aluminum hydroxyhalides, for example, aluminum chlorohydrate, and complexes or mixtures thereof with zirconyl oxyhalides and zirconyl hydroxyhalides, (e.g., aluminum-zirconium chlorohydrate, and aluminum zirconium glycine complexes, such as aluminum zirconium tetrachlorohydrex gly).

In another aspect, the personal care composition is a skin care composition comprising a polymer composition or product described herein, and a vehicle, such as a silicone oil or an organic oil. The skin care composition can also include emollients, such as triglyceride esters, wax esters, alkyl or alkenyl esters of fatty acids or polyhydric alcohol esters, pigments, vitamins (e.g., Vitamin A, Vitamin C and Vitamin E), sunscreen or sunblock compounds (e.g., titanium dioxide, zinc oxide, oxybenzone, octylmethoxy cinnamate, butylmethoxy dibenzoylm ethane, p-aminobenzoic acid and octyl dimethyl-p-aminobenzoic acid).

In yet another aspect, the personal care composition is a color cosmetic composition such as a lipstick, a makeup or mascara. The color cosmetic composition comprises a polymer composition or product described herein and a coloring agent (e.g., pigment, water-soluble dye, or liposoluble dye).

In still yet another aspect, the personal care composition comprises a polymer composition or product described herein and fragrant materials. The fragrant materials can be fragrant compounds, encapsulated fragrant compounds or fragrance releasing compounds that either the neat compounds or are encapsulated.

EXAMPLES

The following synthetic examples (1-22), and formulation examples (F1-F10) and Tables 3-12 are part of the invention, and they are illustrative, but not limiting, of the methods of the present invention. Other suitable modifications and adaptations of the variety of conditions and parameters normally encountered in the field, and which are obvious to those skilled in the art, are within the spirit and scope of the invention.

Synthetic Example 1

A poly(dimethylhydrosiloxy)silicate (8.86 g, 79.74 mmol), silyl undecylenic acid ester (11.97 g, 46.4 mmol), ethyl 10-undecylenate (10.15 g, 47.8 mmol), a vinyl terminal polydimethylsiloxane (45.85 g, 7.97 mmol), hemisqualane (119.79 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (2.3 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 2

A poly(dimethylhydrosiloxy)silicate (8.86 g, 79.74 mmol), silyl undecylenic acid ester (5.25 g, 46.4 mmol), ethyl 10-undecylenate (16.0 g, 75.36 mmol), a vinyl terminal polydimethylsiloxane (45.85 g, 7.97 mmol), hemisqualane (113.94 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.5 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 3

A poly(dimethylhydrosiloxy)silicate (8.86 g, 79.74 mmol), silyl undecylenic acid ester (8.2 g, 31.8 mmol), ethyl 10-undecylenate (13.5 g, 63.5 mmol), a vinyl terminal polydimethylsiloxane (45.85 g, 7.97 mmol), hemisqualane (114.6 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (2.0 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 4

A poly(dimethylhydrosiloxy)silicate (8.86 g, 79.74 mmol), silyl undecylenic acid ester (11.0 g, 42.68 mmol), ethyl 10-undecylenate (13.5 g, 63.5 mmol), a vinyl terminal polydimethylsiloxane (45.85 g, 7.97 mmol), hemisqualane (118.8 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (2.3 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 5

A poly(dimethylhydrosiloxy)silicate (8.86 g, 79.74 mmol), silyl undecylenic acid ester (5.18 g, 19.98 mmol), ethyl 10-undecylenate (13.5 g, 63.5 mmol), a vinyl terminal polydimethylsiloxane (45.85 g, 7.97 mmol), hemisqualane (110.0 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.2 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 6

A poly(dimethylhydrosiloxy)silicate (8.86 g, 79.74 mmol), silyl undecylenic acid ester (2.1 g, 8.1 mmol), ethyl 10-undecylenate (13.5 g, 63.5 mmol), a vinyl terminal polydimethylsiloxane (45.85 g, 7.97 mmol), hemisqualane (105.46 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (0.5 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 7

A poly(dimethylhydrosiloxy)silicate (8.86 g, 79.74 mmol), silyl undecylenic acid ester (5.15 g, 19.98 mmol), heptyl 10-undecylenate (17.6 g, 62.3 mmol), a vinyl terminal polydimethylsiloxane (45.85 g, 7.97 mmol), hemisqualane (116.19 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.2 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 8

A poly(dimethylhydrosiloxy)silicate (8.86 g, 79.74 mmol), silyl undecylenic acid ester (5.15 g, 19.98 mmol), heptyl 10-undecylenate (20.0 g, 70.8 mmol), a vinyl terminal polydimethylsiloxane (45.85 g, 7.97 mmol), hemisqualane (119.79 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.2 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 9

A poly(dimethylhydrosiloxy)silicate (8.86 g, 79.74 mmol), silyl undecylenic acid ester (10.0 g, 38.8 mmol), heptyl 10-undecylenate (14.5 g, 51.3 mmol), a vinyl terminal polydimethylsiloxane (45.85 g, 7.97 mmol), hemisqualane (118.8 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.4 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 10

A poly(dimethylhydrosiloxy)silicate (8.86 g, 79.74 mmol), silyl undecylenic acid ester (10.0 g, 38.8 mmol), heptyl 10-undecylenate (18.5 g, 65.49 mmol), a vinyl terminal polydimethylsiloxane (45.85 g, 7.97 mmol), hemisqualane (124.8 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.4 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 11

A poly(dimethylhydrosiloxy)silicate (8.86 g, 79.74 mmol), silyl undecylenic acid ester (7.5 g, 29.1 mmol), heptyl 10-undecylenate (17.25 g, 61.09 mmol), a vinyl terminal polydimethylsiloxane (45.85 g, 7.97 mmol), hemisqualane (119.19 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.04 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 12

A poly(dimethylhydrosiloxy)silicate (8.86 g, 79.74 mmol), silyl undecylenic acid ester (10 g, 38.8 mmol), heptyl 10-undecylenate (16.0 g, 56.64 mmol), a vinyl terminal polydimethylsiloxane (45.85 g, 7.97 mmol), hemisqualane (121.0 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.4 g) was added, and continued to stir at 85° C. for an hour to free up the silyl protected carboxylic acid. Then the reaction mixture was vacuum stripped at 85° C. and 150 mmHg for 30 minutes when the product was obtained as a viscous oil.

Synthetic Example 13

A poly(dimethylhydrosiloxy)silicate (8.86 g, 79.74 mmol), silyl undecylenic acid ester (10 g, 38.8 mmol), heptyl 10-undecylenate (14.0 g, 49.56 mmol), a vinyl terminal polydimethylsiloxane (45.85 g, 7.97 mmol), hemisqualane (121.0 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.4 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 14

A poly(dimethylhydrosiloxy)silicate (8.86 g, 79.74 mmol), heptyl 10-undecylenate (25.0 g, 88.5 mmol), a vinyl terminal polydimethylsiloxane (45.85 g, 7.97 mmol), hemisqualane (119.56 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and 85° C. for 3 hours when the product was obtained as a viscous gel.

Synthetic Example 15

A poly(dimethylhydrosiloxy)silicate (8.86 g, 79.74 mmol), silyl undecylenic acid ester (2.0 g, 7.76 mmol), heptyl 10-undecylenate (22.0 g, 77.88 mmol), a vinyl terminal polydimethylsiloxane (45.85 g, 7.97 mmol), hemisqualane (118.06 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (0.28 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 16

A poly(dimethylhydrosiloxy)silicate (8.86 g, 79.74 mmol), silyl undecylenic acid ester (7.0 g, 27.16 mmol), heptyl 10-undecylenate (18.0 g, 63.72 mmol), a vinyl terminal polydimethylsiloxane (45.85 g, 7.97 mmol), hemisqualane (119.56 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (1.0 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 17

A polymethylhydrosiloxane (7.5 g, 125 mmol), silyl undecylenic acid ester (5.0 g, 19.4 mmol), heptyl 10-undecylenate (30.0 g, 106.2 mmol), a vinyl terminal polydimethylsiloxane (45.85 g, 7.97 mmol), hemisqualane (132.52 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (0.7 g) was added, and continued to stir at 85° C. for an hour to free up the silyl protected carboxylic acid. Then the reaction mixture was vacuum stripped at 85° C. and 150 mmHg for 30 minutes when the product was obtained as soft gel powder. To this was added Element 14 PDMS 5 cst oil (1400.0 g) and mixed under high shear mixing until a homogeneous gel was obtained.

Synthetic Example 18

A poly(dimethylhydrosiloxy)silicate (7.5 g, 67.5 mmol), silyl undecylenic acid ester (7.18 g, 28.0 mmol), heptyl 10-undecylenate (20.0 g, 70.8 mmol), a vinyl terminal polydimethylsiloxane (90.0 g, 3.96 mmol), hemisqualane (100 g) and platinum(0)-1,3-divinyl-1,1,3,3-tetramethyldisiloxane complex (0.005 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (0.7 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 19

A poly(dimethylhydrosiloxy)silicate (7.5 g, 67.5 mmol), silyl undecylenic acid ester (4.0 g, 15.6 mmol), undecylenic acid (2.3 g, 12.4 mmol), heptyl 10-undecylenate (20.0 g, 70.8 mmol), a vinyl terminal polydimethylsiloxane (90.0 g, 3.96 mmol), hemisqualane (100 g) and platinum(0)-1,3-divinyl-1,1,3,3-tetramethyldisiloxane complex (0.005 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (0.7 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 20

A polydimethylhydrosiloxane (3.75 g, 62.5 mmol), silyl undecylenic acid ester (5.0 g, 19.45 mmol), heptyl 10-undecylenate (25.0 g, 88.5 mmol), a vinyl terminal polydimethylsiloxane (57.5 g, 2.53 mmol), bis methallyl capped poly(ethylene glycol-co-propylene glycol) containing 60% E0 and 40% PO (2.0 g, 1.32 mmol), hemisqualane (150 g) and platinum(0)-1,3-divinyl-1,1,3,3-tetramethyldisiloxane complex (0.002 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (0.7 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 21

A poly(dimethylhydrosiloxy)silicate (7.5 g, 67.5 mmol), silyl undecylenic acid ester (7.0 g, 27.2 mmol), hemisqualane (100 g) and platinum(0)-1,3-divinyl-1,1,3,3-tetramethyldisiloxane complex (0.005 g Pt) were added into a reactor. The reactor was closed and the air inside was replaced by flashing with nitrogen. Then the mixture was stirred at room temperature for an hour and added heptyl 10-undecylenate (20.0 g, 70.8 mmol), a vinyl terminal polydimethylsiloxane (90.0 g, 3.96 mmol) and continued to mix under shear at 85° C. for 3 hours when the entire reaction mixture was transformed into a viscous gel, and then deionized water (0.7 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Synthetic Example 22

A poly(dimethylhydrosiloxy)silicate (7.5 g, 67.5 mmol), silyl undecylenic acid ester (4.0 g, 15.6 mmol), allyloxy (polyethyleneoxide) (6.82 g, 12.4 mmol), heptyl 10-undecylenate (20.0 g, 70.8 mmol), a vinyl terminal polydimethylsiloxane (90.0 g, 3.96 mmol), hemisqualane (100 g) and platinum(0)-1,3-divinyl-1,1,3,3-tetramethyldisiloxane complex (0.005 g Pt) were added into a reactor. The reactor was closed and the air inside was replaced by flashing with nitrogen. Then the mixture was stirred at room temperature for an hour and at 85° C. for 3 hours when the entire reaction mixture was transformed into a viscous gel, and then deionized water (0.7 g) was added, and continued to stir at 85° C. for an hour to free up the silyl protected carboxylic acid. Then the reaction mixture was vacuum stripped at 85° C. and 150 mmHg for 30 minutes when the product was obtained as a viscous gel.

Comparative Example 1

A commercially available traditional silicone gel containing 5 wt % active network were used as benchmark.

Comparative Example 2

Hemisqualane (94.38 g), a poly(dimethylhydrosiloxy)silicate (8.86 g, 79.74 mmol) and silyl undecylenic acid ester (23.94 g, 95.5 mmol) were added into a reactor. To this mixture, platinum(0)-1,3-divinyl-1,1,3,3-tetramethyldisiloxane complex (0.002 g Pt) dissolved in hemisqualane (5 mL) was added. The reactor was closed and the air inside was replaced by flashing with nitrogen. The mixture was continued to slowly stir at room temperature to facilitate the hydrosilylation of poly(dimethylhydrosiloxy)silicate with the undecylenic acid ester. Once the hydrosilylation with undecylenic acid ester was completed, a vinyl terminal polydimethylsiloxane (45.85 g, 7.97 mmol) dissolved in hemisqualane (23.60 g) and platinum(0)-1,3-divinyl-1,1,3,3-tetramethyldisiloxane complex (0.002 g Pt) were added. The reaction temperature was raised to 85° C. and allowed to shear the mixture for additional 3 hours when the entire reaction mixture was transformed into a viscous gel. To this was added deionized water (3.37 g) and continued to stir at 85° C. for an hour. Then the reaction mixture was vacuum stripped at 85° C. and 150 mmHg for 30 minutes when the product was obtained as a transparent gel.

Comparative Example 3

Hemisqualane (300.0 g), a polymethylhydrosiloxane copolymer (24.0 g, 103.2 mmol) and silyl undecylenic acid ester (22.63 g, 88.25 mmol) were added into a reactor. To this mixture, platinum(0)-1,3-divinyl-1,1,3,3-tetramethyldisiloxane complex (0.005 g Pt) dissolved in hemisqualane (5 mL) was added. The reactor was closed and the air inside was replaced by flashing with nitrogen. The mixture was continued to slowly stir at room temperature to facilitate the hydrosilylation of poly(dimethylhydrosiloxy)silicate with the undecylenic acid ester. Once the hydrosilylation with undecylenic acid ester was completed, a vinyl terminal polydimethylsiloxane (206.0 g, 10.3 mmol) and platinum (0)-1,3-divinyl-1,1,3,3-tetramethyldisiloxane complex (0.005 g Pt) were added. The reaction temperature was raised to 85° C. and allowed to shear the mixture for additional 3 hours when the entire reaction mixture was transformed into a viscous gel. To this was added deionized water (6.37 g) and continued to stir at 85° C. for an hour. Then the reaction mixture was vacuum stripped at 85° C. and 150 mmHg for 30 minutes when the product was obtained as a viscous gel.

It is evident from the Tables 1 and 2, the cross-linked silicone gel containing alkyl carboxylic esters has superior compatibility and structuring properties with various natural and synthetic oils compared to traditional and carboxylic acid functional silicone gels. Therefore, these materials can help broadening the applications scope of the silicone gel materials across different products portfolio.

TABLE 1

Compatibility and structuring performance of comparative materials

| Ingredients | Network Content (%) | COOH content (mmol/g) | $COOC_nH_{2n+1}$ content (mmol/g) | CF1 | CF2 | CF3 | CF4 | CF5 | CF6 | CF7 | CF8 | CF9 | CF10 | CF11 | CF12 |
|---|---|---|---|---|---|---|---|---|---|---|---|---|---|---|---|
| Comparative Example 1 | 5 | — | — | 1.0 | 1.0 | 1.0 | 1.0 | | | | | | | | |
| Comparative Example 2 | 40 | 0.477 | — | | | | | 1.0 | 1.0 | 1.0 | 1.0 | | | | |
| Comparative Example 3 | 45 | 0.159 | — | | | | | | | | | 1.0 | 1.0 | 1.0 | 1.0 |
| Element 14 PDMS 5 | — | — | — | 7.0 | 7.0 | 7.0 | 7.0 | | | | | | 4.5 | 4.5 | 4.5 |
| Isononyl Isononanoate | — | — | — | | | | | 9.0 | | | | 9.0 | | | |
| Isopropyl Myristate | — | — | — | | | | | | 9.0 | | | | 4.5 | | |
| Caprylic/ Capric Triglyceride | — | — | — | | | | | | | 9.0 | | | | 4.5 | |

TABLE 1-continued

Compatibility and structuring performance of comparative materials

| Ingredients | Network Content (%) | COOH content (mmol/g) | COOC$_n$H$_{2n+1}$ content (mmol/g) | CF1 | CF2 | CF3 | CF4 | CF5 | CF6 | CF7 | CF8 | CF9 | CF10 | CF11 | CF12 |
|---|---|---|---|---|---|---|---|---|---|---|---|---|---|---|---|
| Dibutyl Adipate | — | — | — | | | | | | | | | 9.0 | | | 4.5 |
| Sunflower Oil | — | — | — | 2.0 | | | | | | | | | | | |
| Jojoba Oil | — | — | — | | 2.0 | | | | | | | | | | |
| Coconut Oil | — | — | — | | | 2.0 | | | | | | | | | |
| Olive Oil | — | — | — | | | | 2.0 | | | | | | | | |
| Total | | | | 10 | 10 | 10 | 10 | 10 | 10 | 10 | 10 | 10 | 10 | 10 | 10 |
| Compatibility | | | | No | No | No | No | No | No | No | No | No | No | No | No |
| Oil Structuring | | | | No | No | No | No | No | No | No | No | No | No | No | No |

TABLE 2

Compatibility and structuring performance of comparative materials

| Ingredients | Network Content | COOH content (mmol/g) | COOC$_n$H$_{2n+1}$ content (mmol/g) | F1 | F2 | F3 | F4 | F5 | F6 | F7 | F8 | F9 | F10 | F11 | F12 |
|---|---|---|---|---|---|---|---|---|---|---|---|---|---|---|---|
| Synthetic Example 8 | 40 | 0.099 | 0.353 | 1.0 | 1.0 | | | | | | | | | | |
| Synthetic Example 9 | 40 | 0.194 | 0.257 | | | 1.0 | 1.0 | | | | | | | | |
| Synthetic Example 14 | 40 | — | 0.444 | | | | | 1.0 | 1.0 | 1.0 | 1.0 | | | | |
| Synthetic Example 15 | 40 | 0.039 | 0.395 | | | | | | | | | 1.0 | 1.0 | | |
| Synthetic Example 16 | 40 | 0.135 | 0.318 | | | | | | | | | | | 1.0 | |
| Synthetic Example 17 | 5 | 0.022 | 0.120 | | | | | | | | | | | | 1.0 |
| Element 14 PDMS 5 | — | — | — | 7.0 | 7.0 | 7.0 | 7.0 | | | | | | 4.5 | 4.5 | 4.5 |
| Isononyl Isononanoate | — | — | — | | | | | 9.0 | | | | 9.0 | | | |
| Isopropyl Myristate | — | — | — | | | | | | | 9.0 | | | 4.5 | | |
| Caprylic/Capric Triglyceride | — | — | — | | | | | | | | 9.0 | | | 4.5 | |
| Dibutyl Adipate | — | — | — | | | | | | | | | 9.0 | | | 4.5 |
| Sunflower Oil | — | — | — | 2.0 | | | | | | | | | | | |
| Jojoba Oil | — | — | — | | 2.0 | | | | | | | | | | |
| Coconut Oil | — | — | — | | | 2.0 | | | | | | | | | |
| Olive Oil | — | — | — | | | | 2.0 | | | | | | | | |
| Total | | | | 10 | 10 | 10 | 10 | 10 | 10 | 10 | 10 | 10 | 10 | 10 | 10 |
| Compatibility | | | | Y | Y | Y | Y | Y | Y | Y | Y | Y | Y | Y | Y |
| Oil Structuring | | | | Y | Y | Y | Y | Y | Y | Y | Y | Y | Y | Y | Y |

Formulation Example 1

Hair Protection Serum.

Procedure:
All of the ingredients were added in a beaker and mixed at room temperature until homogeneous.

TABLE 3

| INGREDIENTS | International Nomenclature of Cosmetic Ingredients (INCI) | Supplier | % w/w |
|---|---|---|---|
| SF 1202 | Cyclopentasiloxane | Momentive | 66.55 |
| Synthetic Example 18 | | | 7.50 |
| Isopropyl myristate | | Croda | 20.00 |
| SilSoft A+ | PEG-40/PPG-8 Methylaminopropyl/ Hydropropyl Dimethicone copolymer | Momentve | 0.50 |
| SilSoft 034 | Caprylyl Methicone | Momentive | 5.00 |
| 20% Aqueous KOH | | | 0.45 |
| Total | | | 100.00 |

Formulation Example 2

Repair Hair Oil.

Procedure:
All of the ingredients were added in a beaker and mixed at room temperature until homogeneous.

TABLE 4

| INGREDIENTS | INCI | Supplier | % w/w |
|---|---|---|---|
| Hemisqualane | C13-15 Alkane | Amyris Inc. | 30.05 |
| SF1202 | Cyclopentasiloxane | Momentive | 50.00 |
| SilSoft 034 | Caprylyl Methicone | Momentive | 10.00 |
| Synthetic Example 18 | | | 7.50 |
| Almond Oil | Prunus amygdalus dulcis (almond) oil | | 1.00 |
| SilSoft CLX-E | Dipropylene Glycol (and) Polysilicone-29 | Momentive | 1.00 |
| 20% Aqueous KOH | | | 0.45 |
| Total | | | 100.00 |

Formulation Example 3

Nourishing Skin Essence.

Procedure:
All of the ingredients were added in a beaker and mixed at room temperature until homogeneous.

TABLE 5

| INGREDIENTS | INCI | Supplier | % w/w |
|---|---|---|---|
| Hemisqualane | C13-15 Alkane | Amyris Inc. | 84.60 |
| Synthetic Example 18 | | | 10.00 |
| Argan Oil | Argania Spinosa Kernel Oil | | 1.00 |
| Olive Oil | Olea Europaea (olive) oil | | 1.00 |
| Jojoba Oil | Simmondsia Chinensis (Jojoba) Seed Oil | | 1.00 |
| Almond Oil | Prunus amygdalus dulcis (almond) oil | | 1.00 |
| Vitamin E Acetate | Tocopheryl Acetate | | 0.50 |
| Fragrance | | | 0.30 |
| 20% Aqueous KOH | | | 0.60 |
| Total | | | 100.00 |

Formulation Example 4

Honey Body Gel.

Procedure:
All of the ingredients were added in a beaker and mixed at room temperature until homogeneous.

TABLE 6

| INGREDIENTS | INCI | Supplier | % w/w |
|---|---|---|---|
| Hemisqualane | C13-15 Alkane | Amyris Inc. | 56.40 |
| Isododecane | Isododecane | Sigma Aldrich | 10.00 |
| SilSoft One | | Momentive | 20.00 |
| Synthetic Example 18 | | | 10.00 |
| Argan Oil | Argania Spinosa Kernel Oil | | 1.00 |
| Pigment | (Mica (and) Titanium Dioxide (and) Iron Oxides) | | 0.70 |
| Tocopherol Acetate | Tocopheryl Acetate | | 1.00 |
| Fragrance | | | 0.30 |
| 20% Aqueous KOH | | | 0.60 |
| Total | | | 100.00 |

Formulation Example 5

Shimmering Body Oil Gel.

Procedure:
All of the ingredients were added in a beaker and mixed at room temperature until homogeneous.

TABLE 7

| INGREDIENTS | INCI | Supplier | % w/w |
|---|---|---|---|
| Hemisqualane | C13-15 Alkane | Amyris Inc. | 57.60 |
| Almond Oil | Prunus amygdalus dulcis (almond) oil | | 5.00 |
| Jojoba Oil | Simmondsia Chinensis (Jojoba) Seed Oil | | 5.00 |
| Synthetic Example 18 | | | 10.00 |
| Mineral Oil | Paraffinum Liquidum | | 20.00 |
| Pigment | Mica (and) Titanium Dioxide (and) Tin oxide | | 0.50 |
| Tocopherol Acetate | Tocopheryl Acetate | | 1.00 |
| Fragrance | | | 0.30 |
| 20% Aqueous KOH | | | 0.60 |
| Total | | | |

Formulation Example 6

Baby Oil Gel.

Procedure:
All of the ingredients were added in a beaker and mixed at room temperature until homogeneous.

TABLE 8

| INGREDIENTS | INCI | Supplier | % w/w |
|---|---|---|---|
| Hemisqualane | C13-15 Alkane | Amyris Inc. | 37.40 |
| SF1202 | Cyclopentasiloxane | Momentive | 20.00 |
| Mineral Oil | Paraffinum Liquidum | | 30.00 |
| Synthetic Example 18 | | | 10.00 |
| Jojoba Oil | Simmondsia Chinensis (Jojoba) Seed Oil | | 1.00 |
| Shea Butter | Butyrospermum Parkii (Shea) Butter | | 0.50 |
| Tocopherol Acetate | Tocopherol Acetate | | 0.50 |
| 20% Aqueous KOH | | | 0.60 |
| Total | | | 100.00 |

Formulation Example 7

Natural Massage Oil

Procedure:
All of the ingredients were added in a beaker and mixed at room temperature until homogeneous.

TABLE 9

| INGREDIENTS | INCI | Supplier | % w/w |
|---|---|---|---|
| Glycerine | Glycerin | Sigma Aldrich | 18.90 |
| Isononyl Isononanoate | Isononyl Isononanoate | | 5.00 |
| Hemisqualane | C13-15 Alkane | Amyris Inc. | 35.00 |
| Synthetic Example 20 | | | 10.00 |
| Sunflower Oil | Helianthus Annuus (Sunflower) Seed Oil | | 20.00 |
| Almond Oil | Prunus amygdalus dulcis (almond) oil | | 5.00 |
| Jojoba Oil | Simmondsia Chinensis (Jojoba) Seed Oil | | 5.00 |
| Tocopherol Acetate | Tocopherol Acetate | | 0.50 |
| 20% Aqueous KOH | | | 0.60 |
| Total | | | 100.00 |

Formulation Example 8

Anhydrous SPF 30 PA+++ Sunscreen Gel

Procedure:
All of the ingredients were added in a beaker and mixed at room temperature until homogeneous.

TABLE 10

| INGREDIENTS | INCI | Supplier | % w/w |
|---|---|---|---|
| SF1202 | Cyclopentasiloxane | Momentive | 14.50 |
| Isododecane | Isododecane | Sigma Aldrich | 25.00 |
| Isononyl Isononanoate | Isononyl Isononanoate | | 10.00 |
| Isopropyl Myristate | Isopropyl Myristate | | 5.00 |
| Synthetic Example 21 | | | 8.50 |
| Octocrylene | Octocrylene | | 10.00 |
| Homosalate | 3,3,5-Trimethylcyclohexyl salicylate | | 10.00 |
| Ethylhexyl Salicylate | 2-Ethylhexyl salicylate | | 5.00 |
| Octyl-methoxycinnamate | Octyl methoxycinnamate | | 7.50 |
| Avobenzone | Butyl Methoxydibenzoylmethane | | 3.00 |
| Tocopherol Acetate | Tocopherol Acetate | | 0.50 |
| Boron Nitride | Boron Nitride | | 1.00 |
| 20% Aqueous KOH | | | 0.51 |
| Total | | | 100.00 |

Formulation Example 9

Natural Tinted Lip Balm.

Procedure:
All of the ingredients were added in a beaker and mixed at room temperature until homogeneous.

TABLE 11

| INGREDIENTS | INCI | Supplier | % w/w |
|---|---|---|---|
| Hemisqualane | C13-15 Alkane | Amyris Inc. | 32.30 |
| Isododecane | Isododecane | | 10.00 |
| Castor Oil | Ricinus communis (Castor) Seed Oil | | 20.00 |
| Synthetic Example 18 | | | 15.00 |
| Sunflower Oil | Helianthus Annuus (Sunflower) Seed Oil | | 20.00 |
| Tocopherol Acetate | Tocopherol Acetate | | 0.50 |
| Pigment | Mica (and) Titanium Dioxide (and) Tin oxide | | 1.00 |
| Fragrance | | | 0.30 |
| 20% Aqueous KOH | | | 0.90 |
| Total | | | 100.00 |

Formulation Example 10

Anhydrous HD Foundation

Procedure:
All of the ingredients were added in a beaker and mixed at room temperature until homogeneous.

TABLE 12

| INGREDIENTS | INCI | Supplier | % w/w |
|---|---|---|---|
| Isododecane | Isododecane | Sigma-Aldrich | 51.65 |
| Synthetic Example 21 | | | 10.00 |
| Isononyl Isononanoate | Isononyl Isononanoate | | 10.00 |
| TiO$_2$ | Titanium dioxide | | 7.00 |
| Red Iron Oxide | Iron Oxide | | 0.50 |
| Yellow | Iron Oxide | Iron Oxide | 0.80 |
| Black Iron Oxide | Iron Oxide | | 0.05 |
| SS 4230 | Cyclopentasiloxane (and) Trimethylsiloxysilicate | Momentive | 3.00 |
| Velvesil 125 | Cyclopentasiloxane (and) C30-45 Alkyl Cetearyl Dimethicone | Momentive | 15.00 |
| Tospearl 3000 | Polymethylsilsesquioxane | Momentive | 2.00 |
| 20% Aqueous KOH | | | 0.60 |
| Total | | | 100.00 |

What is claimed is:

1. A composition comprising a polymer having branched silicone substituted by at least one alkylcarbonylalkyl group and by at least one alkylcarboxy group, and cross-linked with an alkenyl functional cross-linker, wherein an average number of alkylcarboxyalkyl substitutions per silicone is between 1 and 60 and an average number of crosslinks between branched silicones is between 1 and 30.

2. The composition of claim 1, wherein the average number of alkylcarboxyalkyl substitutions per silicone is between 1 and 15.

3. The composition of claim 1, wherein the average number of crosslinks between branched silicones is between 1 and 15.

4. The composition of claim 1, wherein the polymer is prepared by a method comprising reacting:

(a) a Si—H functional compound of formula (I):

$$M^H{}_a M_b D^H{}_c D_d T^H{}_e T_f Q_g \quad (I)$$

wherein:
$M^H = R^1 R^2 HSiO_{1/2}$;
$M = R^3 R^4 R^5 SiO_{1/2}$;
$D^H = R^6 HSiO_{2/2}$;
$D = R^7 R^8 SiO_{2/2}$;
$T^H = HSiO_{3/2}$;
$T = R^9 SiO_{3/2}$; and
$Q = SiO_{4/2}$;

wherein
$R^1, R^2, R^3, R^4, R^5, R^6, R^7, R^8$, and $R^9$ are independently an aliphatic, aromatic, or fluoro monovalent hydrocarbon having from 1 to 60 carbon atoms; and a, b, c, d, e, f, and g are independently zero or a positive integer, such that $2 \leq a+b+c+d+e+f+g \leq 6000$ and when $a'+c'+e'=2$, $a+c+e>2$ and wherein $e+f+g \geq 1$;

(b) a carboxy functional olefin of formula (II):

$$\text{//}\!-\![CH_2]_n\!-\!COOR' \quad (II)$$

wherein
R' is a combination of $R^1$ and $—Si(R^a)_3$, wherein $R^1$ is a $C_1$-$C_{60}$ monovalent hydrocarbon and $R^a$ is an aliphatic, aromatic, or fluoro monovalent hydrocarbon; and
n is $0 \leq n \leq 30$; and (c) a silicone based alkenyl functional cross-linker of formula (III) and/or a non-silicone based alkenyl functional cross-linker of formula (IV):

$$M^1{}_{a'} M^2{}_{b'} D^1{}_{c'} D^2{}_{d'} T^1{}_{e'} T^2{}_{f'} Q_{g'} \quad (III)$$

$$\text{//}\!-\!Z\!-\!\backslash\backslash \quad (IV)$$

wherein:
$M^1 = R^{10} R^{11} R^{12} SiO_{1/2}$;
$M^2 = R^{13} R^{14} R^{15} SiO_{1/2} O$;
$D^1 = R^{16} R^{17} SiO_{2/2}$;
$D^2 = R^{18} R^{19} SiO_{2/2}$;
$T^1 = R^{20} SiO_{3/2}$;
$T^2 = R^{21} SiO_{3/2}$; and
$Q = SiO_{4/2}$;

wherein
$R^{11}, R^{12}, R^{13}, R^{14}, R^{15}, R^{17}, R_{18}, R^{19}$, and $R^{21}$, are independently an aliphatic, aromatic, or fluoro monovalent hydrocarbon having from 1 to 60 carbon atoms;
$R^{10}, R^{16}$, and $R^{20}$ are each a monovalent radical containing at least one terminal olefin bond; a', b', c', d', e', f', and g' are independently zero or a positive integer, such that $2 \leq a'+b'+c'+d'+e'+f'+g' \leq 6000$ and when $a+c+e=2$, $a'+c'+e'>2$; and
Z is $—(CHR^{22})_m—$ or $—(CH_2CHR^{23}O)_k—$, wherein m and k are positive integers, such that $1 \leq m \leq 60$ and $1 \leq k \leq 500$, and $R^{22}$ and $R^{23}$ are independently hydrogen or monovalent hydrocarbon having from 1 to 60 carbon atoms.

5. The composition of claim 4, wherein the one or more of $R^1, R^2, R^3, R^4, R^5, R^6, R^7, R^8$, and $R^9$ is a $C_1$-$C_{20}$ monovalent hydrocarbon.

6. The composition of claim 4, wherein a, b, c, d, e, f, and g are $2 \leq a+b+c+d+e+f+g$: $\leq 4000$.

7. The composition of claim 4, wherein one or more of $R^{11}, R^{12}, R_{13}, R^{14}, R^{15}, R^{17}, R^{18}, R^{19}$, and $R^{21}$ is a $C_1$-$C_{30}$ monovalent hydrocarbon.

8. The composition of claim 4, wherein one or more of $R^{11}, R^{12}, R^{13}, R^{14}, R^{15}, R^{17}, R^{18}, R^{19}$, and $R^{21}$ is an aromatic monovalent hydrocarbon.

9. The composition of claim 4, wherein one or more of $R^{11}, R^{12}, R^{13}, R^{14}, R^{15}, R^{17}, R^{18}, R^{19}$, and $R^{21}$ is a fluoro monovalent hydrocarbon.

10. A method for preparing a polymer having branched silicone comprising reacting:

(a) a Si—H functional compound of formula (I):

$$M^H{}_a M_b D^H{}_c D_d T^H{}_e T_f Q_g \quad (I)$$

wherein:
$M^H = R^1 R^2 HSiO_{1/2}$;
$M = R^3 R^4 R^5 SiO_{1/2}$;
$D^H = R^6 HSiO_{2/2}$;
$D = R^7 R^8 SiO_{2/2}$;
$T^H = HSiO_{3/2}$;
$T = R^9 SiO_{3/2}$; and
$Q = SiO_{4/2}$;

wherein
$R^1, R^2, R^3, R^4, R^5, R^6, R^7, R^8$, and $R^9$ are independently an aliphatic, aromatic, or fluoro monovalent hydrocarbon having from 1 to 60 carbon atoms; and
a, b, c, d, e, f, and g are independently zero or a positive integer, such that $2 \leq a+b+c+d+e+f+g \leq 6000$ and when $a'+c'+e'=2$, $a+c+e>2$ and wherein $e+f+g \geq 1$;

(b) a carboxy functional olefin of formula (II):

$$\text{//}\!-\![CH_2]_n\!-\!COOR' \quad (II)$$

wherein
R' is a combination of $R^1$ and $—Si(R^a)_3$, wherein $R^1$ is an aliphatic, aromatic, or fluoro monovalent hydrocarbon having from 1 to 60 carbon atoms and $R^a$ is an aliphatic, aromatic, or fluoro monovalent hydrocarbon, and;
n is $0 \leq n \leq 30$; and (c) a silicone based alkenyl functional cross-linker of formula (III) and/or a non-silicone based alkenyl functional cross-linker of formula (IV):

$$M^1{}_{a'} M^2{}_{b'} D^1{}_{c'} D^2{}_{d'} T^1{}_{e'} T^2{}_{f'} Q_{g'}$$

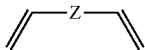
(IV)

wherein:
$M^1 = R^{10}R^{11}R^{12}SiO_{1/2}$;
$M^2 = R^{13}R^{14}R^{15}SiO_{1/2}$;
$D^1 = R^{16}R^{17}SiO_{2/2}$;
$D^2 = R^{18}R^{19}SiO_{2/2}$;
$T^1 = R^{20}SiO_{3/2}$;
$T^2 = R^{21}SiO_{3/2}$; and
$Q = SiO_{4/2}$;
wherein
- $R^{11}$, $R^{12}$, $R^{13}$, $R^{14}$, $R^{15}$, $R^{17}$, $R^{18}$, $R^{19}$, and $R^{21}$, are independently an aliphatic, aromatic, or fluoro monovalent hydrocarbon having from 1 to 60 carbon atoms;
- $R^{10}$, $R^{16}$, $R^{20}$ and are each a monovalent radical containing at least one terminal olefin bond;
- a', b', c', d', e', f', and g' are independently zero or a positive integer, such that 2≤a'+b'+c'+d'+e'+f+g'≤6000 and when a+c+e=2, a'+c'+e'>2;
- Z is —(CHR$_{22}$)$_m$— or —(CH$_2$CHR$^{23}$O)$_k$—, wherein m and k are positive integers, such that 1≤m≤60 and 1≤k≤500, and $R^{22}$ and $R^{23}$ are independently hydrogen or monovalent hydrocarbon having from 1 to 60 carbon atoms; and
- wherein an average number of crosslinks between branched silicones is between 1 and 30.

11. The method of claim 10, wherein one or more of $R^1$, $R^2$, $R^3$, $R^4$, $R^5$, $R^6$, $R^7$, $R^8$, and $R^9$ is a $C_1$-$C_{20}$ monovalent hydrocarbon.

12. The method of claim 10, wherein one or more $R^{11}$, $R^{12}$, $R^{13}$, $R^{14}$, $R^{15}$, $R^{17}$, $R^{18}$, $R^{19}$, and $R^{21}$ is a $C_1$-$C_{60}$ monovalent hydrocarbon.

13. The method of claim 10, wherein the reaction between the Si—H compound of formula (I), the carboxy functional olefin of formula (II) and the alkenyl functional cross-linker of formula (III) and/or (IV) occurs in the presence of at least one precious metal catalyst selected from the group consisting of a rhodium, ruthenium, palladium, osmium, iridium, iron and platinum catalyst.

14. A personal care composition comprising:
(a) the composition of claim 1; and
(b) one or more personal care components.

15. The composition of claim 4, wherein the method further comprises deprotecting the silyl protected carboxylic acid.

16. The method of claim 10, wherein the method further comprises deprotecting the silyl protected carboxylic acid.

17. The composition of claim 4, wherein a=12; b, c, d, e, and f=0; and g=10.

18. The composition of claim 4, wherein a=3; b, c, d, e, and g=0; and f=1.

* * * * *